US00PP19404P2

(12) United States Plant Patent
Valstar

(10) Patent No.: US PP19,404 P2
(45) Date of Patent: Nov. 4, 2008

(54) ***CALATHEA* PLANT NAMED 'HGV03'**

(50) Latin Name: *Calathea rosea-picta*
Varietal Denomination: HGV03

(75) Inventor: Oscar R. Valstar, Maasland (NL)

(73) Assignee: Gebr. Valstar Beheer BV, Maasland (NL)

( * ) Notice: Subject to any disclaimer, the term of this patent is extended or adjusted under 35 U.S.C. 154(b) by 0 days.

(21) Appl. No.: 11/716,706

(22) Filed: Mar. 9, 2007

(51) Int. Cl.
*A01H 5/00* (2006.01)

(52) U.S. Cl. ..... Plt./375
(58) Field of Classification Search ..... Plt./375
See application file for complete search history.

(56) References Cited

PUBLICATIONS

UPOV–ROM GTITM, Plant Variety Database, Apr. 2007, GTI Jouve Retireval Software, citation for calathea, 'HGVO3'.*

* cited by examiner

*Primary Examiner*—Annette H Para
*Assistant Examiner*—S. B. McCormick-Ewoldt

(57) ABSTRACT

A new cultivar of *Calathea* plant named 'HGV03' that is characterized by variegated leaves on the upper side that are dark green with a light green midrib and double light green circles along the margin and light green spots. The lower side of the leaves are dark red-purple.

1 Drawing Sheet

Botanical Classification: *Calathea rosea-picta.*
Variety Denomination: 'HGV03'.

BACKGROUND OF THE INVENTION

The present invention relates to a new and distinct cultivar of *Calathea* plant botanically known as *Calathea rosea-picta* and hereinafter referred to by the cultivar name 'HGV03'.

The new cultivar was discovered as a single plant by the inventor in a cultivated area of Roosendaal, The Netherlands in October of 2004. 'HGV03' was discovered as a naturally occurring whole plant mutation within a population of unnamed *Calathea rosea-picta* plants in a greenhouse environment.

Asexual reproduction by division of the new cultivar 'HGV03' was first performed in February of 2005 in Roosendaal, The Netherlands. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Calathea* cultivar 'HGV03'.

1. Calathea 'HGV03' exhibits variegated leaves on the upper side that are mainly dark green with a light green midrib and double light green circles along the margin and light green spots.
2. Calathea 'HGV03' exhibits leaves that are dark red-purple on the lower side.

The closest comparison cultivar is *Calathea rosea-picta* 'Illustris'. The new cultivar 'HGV03' is distinguishable from 'Illustris' by the following characteristics:

1. 'HGV03' has leaves with smaller light green spots on the upper side.

2. 'HBV03' has darker colored leaves.
3. 'HBV03' has leaves with double light green circles along the margin of the upper side. The leaves of 'Illustris' have only a single light green circle.

The new cultivar 'HGV03' is distinguishable from the parent plant by the following characteristics:

1. 'HGV03' has leaves with smaller light green spots on the upper side.

BRIEF DESCRIPTION OF THE DRAWING

The accompanying photograph illustrates the distinguishing traits of *Calathea* 'HGV03'. The plant in the photograph shows an overall view of a 30 week old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Calathea* cultivar named 'HGV03'. Data was collected in Maasland, The Netherlands from 30 week old greenhouse grown plants in 13 cm containers. The time of year was Winter and the average temperature was 21 degrees Centigrade during the day and 20 degrees Centigrade at night. No photoperiodic treatments or growth retardants were used. Color determinations are in accordance with the Royal Horticultural Society Colour Chart 2001 edition, except where general color terms of ordinary dictionary significance are used. The growing requirements are similar to the species. 'HGV03' has not been tested under all possible conditions and phenotypic differences may be observed with variations in environmental, climatic, and cultural conditions, however, without any variance in genotype.

Botanical classification: *Calathea* 'HGV03'.
Use: Ornamental.
Parentage: 'HGV03' is a naturally occurring whole plant mutation of an unknown *Calathea rosea-picta* cultivar.
Vigor: Moderate.
Growth rate: Moderate to slow.
Growth habit: Moderately branching from base.
Plant shape: Flattened globose.
Suitable container size: 13 cm diameter container.
Height: Average 23.4 cm in height.
Width: Average 35.2 cm in width.
Hardiness: USDA Zone 10.
Propagation: Division.
Number of divisions or clumps per year: 2.
Time to produce a rooted cutting: Approximately 10 days in the Summer and Winter.
Time to produce a young plant: Approximately 90 days in the Summer and 110 days in the Winter.
Root system: Thick and fibrous.
Stem: No stems, leaves grow directly from base; average 5 clumps.
Foliage:

*Texture.*—Both surfaces smooth, glossy and leathery.
*Leaf arrangement.*—Alternate, growing from the base.
*Compound or single.*—Single.
*Leaf shape.*—Oval to broad oval.
*Leaf apex.*—Short apiculate.
*Leaf base.*—Obtuse.
*Leaf length.*—Average 14.5 cm in length.
*Leaf width.*—10.3 cm in width.
*Quantity of leaves per clump.*—Average 4.
*Pubescence.*—No leaf pubescence.
*Leaf margin.*—Entire, slightly wavy, average 16 waves per leaf (8 on each side.)
*Vein pattern.*—Pinnate.
*Young leaf color* (*upper surface*).—Margins 147A, inner margin 146B; secondary inner margin has a ring of blotches that are 150D. Leaf blade 146A, has irregularly variegated areas on and in between the secondary veins colored in between 150D and 160D.
*Young leaf color* (*lower surface*).—N186C; in areas that are variegated on the upper side are 59D.
*Mature leaf color* (*upper surface*).—Margins in between 139A and 147A, inner margin 143A to 143B; secondary inner margin has a ring that is 145C. Leaf blade in between 139A and 147A, with irregularly variegated areas on or in between the secondary veins, colored 144C.
*Mature leaf color* (*lower surface*).—N186C, in areas that are variegated on the upper side, 59C to 59D.
*Vein color* (*lower surface*).—144C to 144D.
*Vein color* (*upper surface*).—165A.
*Leaf attachment.*—Petiolate.
*Petiole dimensions.*—Average 13.1 cm in length including geniculum, 4 mm in distal diameter, 5 mm in proximal diameter.
*Petiole aspect.*—Rounded, smooth, and glossy.
*Petiole surface.*—Smooth, glossy.
*Petiole color.*—200B, base 183B.
*Geniculum dimensions.*—Average 2.5 cm in length and 4.5 mm in diameter.
*Geniculum color.*—148A.
*Wing dimensions.*—Average 7.1 cm in length and 7 mm in diameter.
*Wing color.*—187C.
*Durability of foliage to stress.*—Moderate to high.

Flowers: Flowers have not been observed.
Disease and insect resistance: Plants of the new *Calathea* have not been observed for disease or insect resistance.

It is claimed:

1. A new and distinct variety of *Calathea* plant named 'HGV03' as described and illustrated.

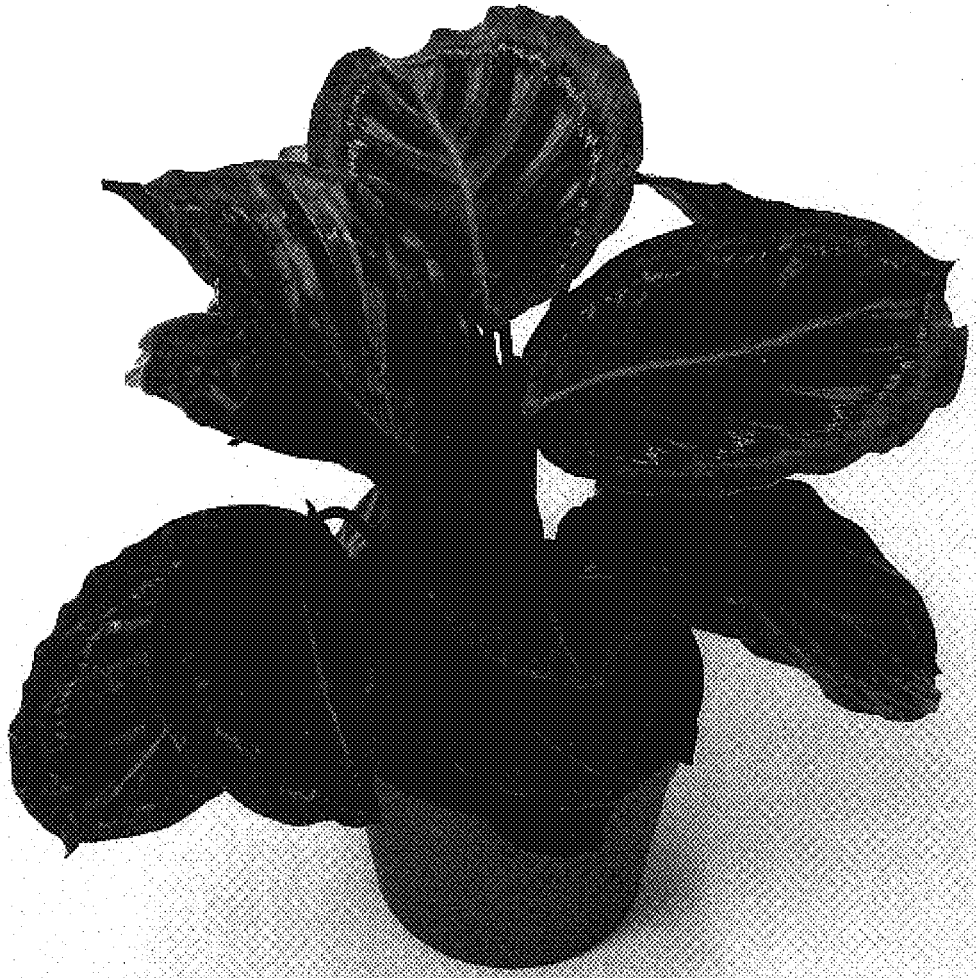

* * * * *